(12) United States Patent
Morrisey et al.

(10) Patent No.: US 12,023,261 B2
(45) Date of Patent: Jul. 2, 2024

(54) OFFSET ADJUSTABLE NECK LENGTH TRIAL DEVICE AND SYSTEM FOR HIP ARTHROPLASTY

(71) Applicants: Stephen Patrick Morrisey, Houston, TX (US); Robert James Jones, Cedar Park, TX (US)

(72) Inventors: Stephen Patrick Morrisey, Houston, TX (US); Robert James Jones, Cedar Park, TX (US)

(73) Assignee: Stephen Patrick Morrisey, Houston, TX (US)

( * ) Notice: Subject to any disclaimer, the term of this patent is extended or adjusted under 35 U.S.C. 154(b) by 300 days.

(21) Appl. No.: 17/733,355

(22) Filed: Apr. 29, 2022

(65) Prior Publication Data

US 2022/0346977 A1 Nov. 3, 2022

Related U.S. Application Data

(60) Provisional application No. 63/181,493, filed on Apr. 29, 2021.

(51) Int. Cl.
*A61F 2/46* (2006.01)
*A61F 2/36* (2006.01)

(52) U.S. Cl.
CPC .......... *A61F 2/4684* (2013.01); *A61F 2/367* (2013.01); *A61F 2002/3611* (2013.01); *A61F 2002/3625* (2013.01); *A61F 2002/365* (2013.01)

(58) Field of Classification Search
CPC .............................. A61F 2/4684; A61F 2/367; A61F 2002/3611; A61F 2002/3625; A61F 2/365;

(Continued)

(56) References Cited

U.S. PATENT DOCUMENTS

| 3,815,590 A | 6/1974 | Deyerle |
| 5,156,624 A | 10/1992 | Barnes |

(Continued)

FOREIGN PATENT DOCUMENTS

| EP | 1679051 | 7/2006 |
| EP | 2241292 | 10/2010 |

(Continued)

OTHER PUBLICATIONS

International Search Report and Written Opinion, Application No. PCT/US2022/026912, dated Aug. 8, 2022.

*Primary Examiner* — Alvin J Stewart
(74) *Attorney, Agent, or Firm* — MacMillan, Sobanski & Todd, LLC

(57) ABSTRACT

Improved hip arthroplasty trial devices and hip arthroplasty trial systems are described. A hip arthroplasty trial device has a head member having a central axis and defining an inner chamber, a head member opening providing access to the inner chamber, and a cavity extending inward from the outer surface of the head member. A rotatable member is disposed in the inner chamber and along an axis between the central axis and one side of the head member. The cavity extends along an axis between the central axis and another, opposite side of the head member. A spacer is disposed within the head member opening and is moveable between a spacer first position and a spacer second position. Rotational movement of the rotatable member moves the spacer from the spacer first position to the spacer second position.

20 Claims, 18 Drawing Sheets

(58) Field of Classification Search
CPC .......... A61F 2/468; A61F 2/3609; A61F 2/36; A61F 2002/30616
See application file for complete search history.

(56) References Cited

U.S. PATENT DOCUMENTS

| | | | |
|---|---|---|---|
| 5,569,263 A * | 10/1996 | Hein | A61B 17/1659 606/85 |
| 5,766,261 A | 6/1998 | Neal et al. | |
| 5,800,556 A | 9/1998 | Sanders et al. | |
| 5,888,211 A * | 3/1999 | Sanders | A61F 2/4684 623/22.4 |
| 6,592,619 B2 * | 7/2003 | Melvin | A61M 60/148 600/16 |
| 6,988,982 B2 * | 1/2006 | Melvin | A61F 2/2481 623/3.16 |
| 7,179,291 B2 | 2/2007 | McLean | |
| 7,273,499 B2 | 9/2007 | McCleary et al. | |
| 7,306,629 B2 | 12/2007 | Saladino et al. | |
| 7,425,214 B1 * | 9/2008 | McCarthy | A61F 2/4684 606/89 |
| 7,485,089 B2 * | 2/2009 | Lau | A61F 2/2481 29/557 |
| 7,601,117 B2 * | 10/2009 | Kute | A61B 17/083 600/16 |
| 7,608,112 B1 | 10/2009 | Kuczynski et al. | |
| 7,959,639 B1 | 6/2011 | McGovern et al. | |
| 8,092,466 B2 | 1/2012 | Splieth et al. | |
| 8,579,985 B2 | 11/2013 | Podolsky et al. | |
| 8,858,623 B2 * | 10/2014 | Miller | A61F 2/2448 623/2.36 |
| 9,168,156 B2 | 10/2015 | Crabtree et al. | |
| 9,265,608 B2 * | 2/2016 | Miller | A61F 2/2445 |
| 9,615,943 B2 | 4/2017 | Brown et al. | |
| 9,775,709 B2 * | 10/2017 | Miller | A61F 2/2445 |
| 10,245,163 B2 | 4/2019 | Davenport et al. | |
| 10,363,136 B2 * | 7/2019 | Miller | A61F 2/2448 |
| 10,596,005 B2 * | 3/2020 | Noel | A61F 2/32 |
| 11,129,733 B2 * | 9/2021 | Morrisey | A61F 2/3609 |
| 11,197,759 B2 * | 12/2021 | Miller | A61F 2/2448 |
| 11,224,517 B2 * | 1/2022 | Langhorn | A61F 2/3609 |
| 11,331,192 B2 * | 5/2022 | Noel | A61L 27/3604 |
| 11,660,213 B2 * | 5/2023 | Morrisey | A61F 2/3609 623/22.42 |
| 2001/0051831 A1 | 12/2001 | Subba Rao et al. | |
| 2002/0193882 A1 | 12/2002 | Koller | |
| 2004/0267372 A1 | 12/2004 | Vanasse et al. | |
| 2005/0143828 A1 | 6/2005 | Collins et al. | |
| 2006/0004249 A1 * | 1/2006 | Kute | A61B 17/083 606/151 |
| 2006/0241748 A1 * | 10/2006 | Lee | A61F 2/2445 623/2.37 |
| 2008/0262609 A1 * | 10/2008 | Gross | A61F 2/2445 623/2.38 |
| 2009/0043397 A1 | 2/2009 | Park | |
| 2009/0054993 A1 | 2/2009 | Le Bon et al. | |
| 2009/0248148 A1 * | 10/2009 | Shaolian | A61F 2/2442 623/2.37 |
| 2010/0023117 A1 * | 1/2010 | Yoganathan | A61F 2/2457 623/2.37 |
| 2011/0166649 A1 * | 7/2011 | Gross | A61F 2/2466 623/2.36 |
| 2011/0247229 A1 * | 10/2011 | Anapliotis | A61F 2/4684 33/512 |
| 2013/0325132 A1 | 12/2013 | Reignier et al. | |
| 2014/0012388 A1 | 1/2014 | Brownhill et al. | |
| 2015/0018961 A1 | 1/2015 | Huddle et al. | |
| 2015/0250620 A1 | 9/2015 | Brown et al. | |
| 2015/0289890 A1 * | 10/2015 | Chen | A61F 2/4684 606/102 |
| 2016/0030199 A1 | 2/2016 | Hunt et al. | |
| 2016/0262912 A1 * | 9/2016 | Burnikel | A61F 2/4684 |
| 2018/0092760 A1 * | 4/2018 | Sperling | A61F 2/4684 |
| 2018/0116823 A1 * | 5/2018 | Johannaber | A61F 2/4657 |
| 2020/0352742 A1 | 11/2020 | Horne et al. | |
| 2022/0047391 A1 * | 2/2022 | Vogt | A61F 2/3094 |
| 2022/0233337 A1 * | 7/2022 | Dmuschewsky | A61F 2/3601 |
| 2022/0241092 A1 * | 8/2022 | Board | A61F 2/3609 |

FOREIGN PATENT DOCUMENTS

| | | |
|---|---|---|
| EP | 1686930 | 4/2011 |
| EP | 1437106 | 4/2013 |
| EP | 2856979 | 3/2017 |
| GB | 1470921 | 4/1977 |
| JP | 3172112 U | 11/2011 |
| WO | WO2003094803 | 11/2003 |
| WO | WO2005072231 | 8/2005 |
| WO | WO2009023971 | 2/2009 |
| WO | WO2010048156 | 4/2010 |
| WO | WO2011063123 | 5/2011 |
| WO | WO2011073351 | 6/2011 |
| WO | WO2015083116 | 6/2015 |
| WO | WO2018149599 | 8/2018 |
| WO | WO2018189125 | 10/2018 |
| WO | WO2018189126 | 10/2018 |
| WO | WO2018189128 | 10/2018 |
| WO | WO2019034769 | 2/2019 |
| WO | WO2019038026 | 2/2019 |
| WO | WO2019038032 | 2/2019 |
| WO | WO2019057698 | 3/2019 |
| WO | 2020223151 A1 | 11/2020 |

* cited by examiner

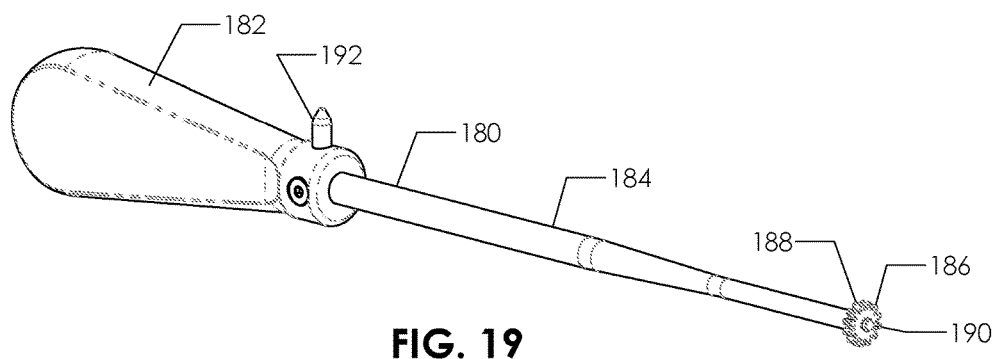
FIG. 19
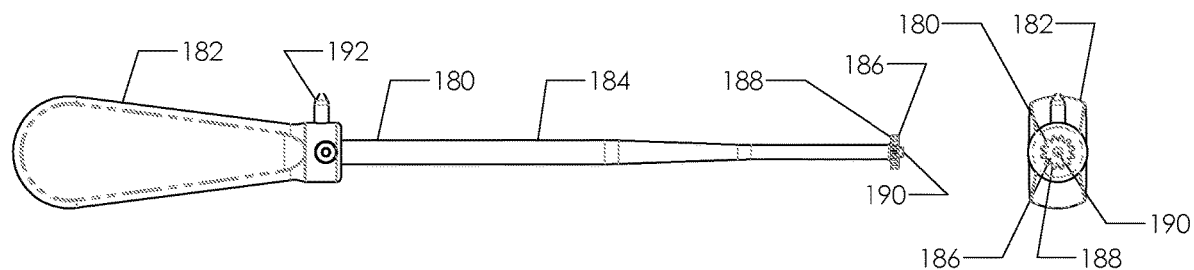
FIG. 20
FIG. 21

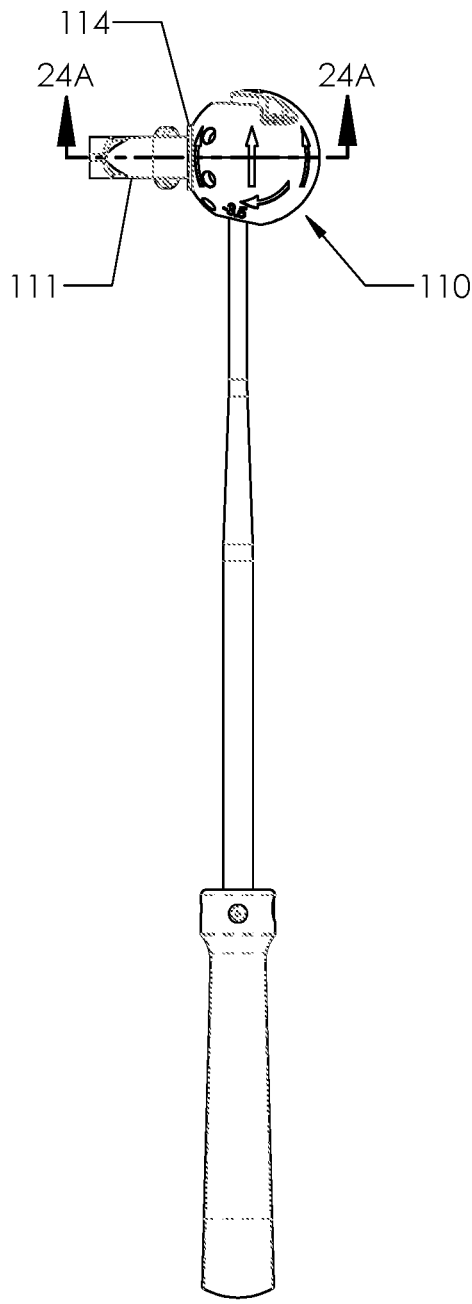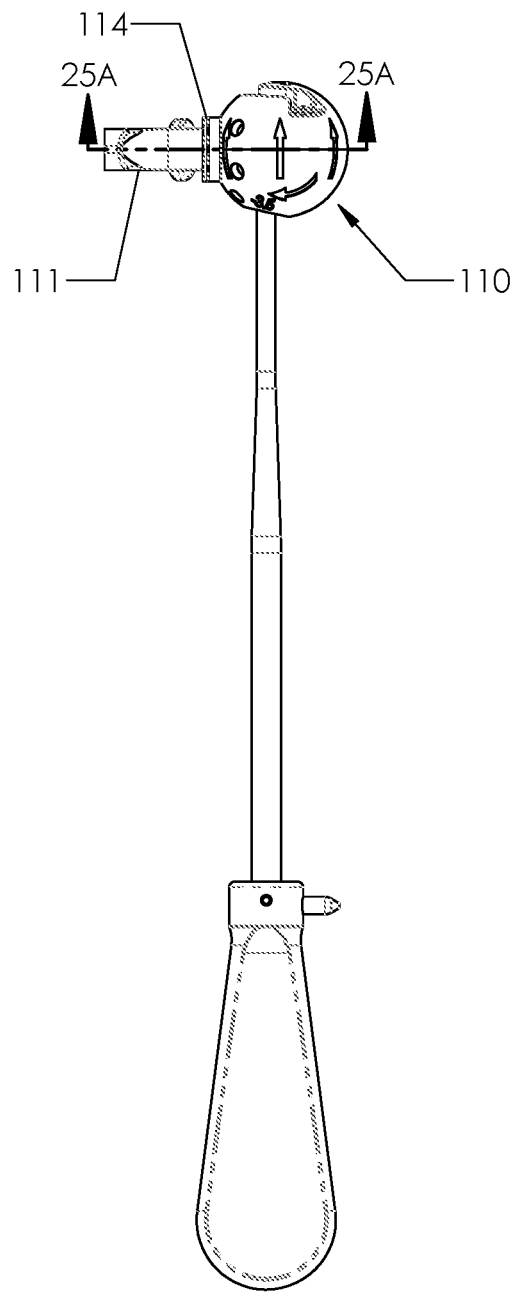
FIG. 24
FIG. 25
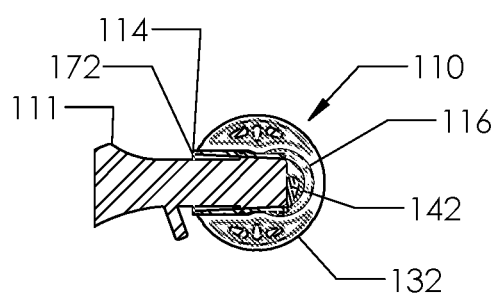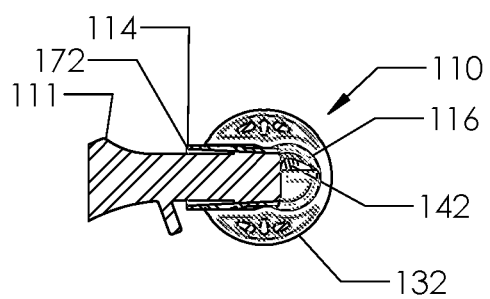
FIG. 24A
FIG. 25A

OFFSET ADJUSTABLE NECK LENGTH TRIAL DEVICE AND SYSTEM FOR HIP ARTHROPLASTY

RELATED APPLICATION

This application claims benefit of U.S. Provisional Application No. 63/181,493, filed on Apr. 29, 2021. The disclosure of this related application is hereby incorporated into this disclosure in its entirety.

FIELD

The disclosure relates to the field of medical devices. More particularly, the disclosure relates to hip arthroplasty trial devices and hip arthroplasty trial systems.

BACKGROUND

When implanting a femoral head during a hip arthroplasty procedure, surgeons currently utilize multiple head length options, which must be individually trialed, to determine the desired offset between the femoral head and a femoral stem. Each trial requires assembly and disassembly of the different head lengths to determine whether a desired offset has been achieved, which results in the hip being dislocated and relocated numerous times during the trial procedure. This multiple trial approach to determining a desired offset between a femoral head implant and a femoral stem has significant drawbacks, such as being complex, time consuming, and disrupting tissue.

Hip arthroplasty is a challenging and complex procedure that often provides limited space for maneuvering and manipulating components. Changing trial devices requires undesirable movement of multiple trial devices into and out of this environment. Even manipulating existing adjustable trial devices can present a challenge considering the limited space available during the procedure.

A need exists, therefore, for new and improved hip arthroplasty trial devices and hip arthroplasty trial systems.

BRIEF SUMMARY OF SELECTED EXAMPLES

Various hip arthroplasty trial devices and hip arthroplasty trial systems are described herein.

An example hip arthroplasty trial device comprises a head member, a spacer disposed in and movable within an opening defined by the head member, a rotatable member defining a gear and a cam adapted to translate the spacer upon rotation of the rotatable member, a drive gear having teeth that mesh with teeth of the gear defined by the rotatable member, and a locking member.

Another example hip arthroplasty trial device comprises a head member, a spacer disposed in and movable within an opening defined by the head member, a rotatable member defining a gear and a cam adapted to translate the spacer upon rotation of the rotatable member, a drive gear having teeth that mesh with teeth of the gear defined by the rotatable member, and a locking member. The drive gear is positioned between a central longitudinal axis of the head member and a proximal side of the head member, which defines the opening within which the spacer is disposed. The gear defined by the rotatable member is positioned between the central longitudinal axis of the head member and a distal side of the head member.

Another example hip arthroplasty trial device comprises a head member, a spacer, a rotatable member, a drive gear, an o-ring disposed on the spacer, and a locking member. The rotatable member defines a cam adapted to translate the spacer upon rotation of the rotatable member. The head member comprises separable first and second head member portions. The rotatable member defines first and second bosses the seat in corresponding grooves of the first and second head member portions, respectively. The first boss defines a gear having teeth that mesh with teeth of the gear defined by the rotatable member. The second boss defines a series of pockets that receive projections defined by the locking member. The drive gear is positioned between a central longitudinal axis of the head member and a proximal side of the head member, which defines the opening within which the spacer is disposed. The gear defined by the rotatable member is positioned between the central longitudinal axis of the head member and a distal side of the head member.

Another example hip arthroplasty trial device comprises a head member, a spacer disposed in and movable within an opening defined by the head member, a rotatable member defining a gear and a cam adapted to translate the spacer upon rotation of the rotatable member, and a locking member. The head member defines a cavity providing access to the gear defined by the rotatable member.

Another example hip arthroplasty trial device comprises a head member, a spacer disposed in and movable within an opening defined by the head member, a rotatable member defining a gear and a cam adapted to translate the spacer upon rotation of the rotatable member, and a locking member. The head member defines a cavity providing access to the gear defined by the rotatable member. The cavity is positioned between a central longitudinal axis of the head member and a proximal side of the head member, which defines the opening within which the spacer is disposed. The gear defined by the rotatable member is positioned between the central longitudinal axis of the head member and a distal side of the head member.

Another example hip arthroplasty trial device comprises a head member having a central axis, defining an inner chamber, and having a head member outer surface, a head member proximal side, and a head member distal side, the head member outer surface defining a head member cavity extending into the head member and along an axis between the central axis and the head member proximal side, the head member proximal side defining a head member opening that provides access to the inner chamber; a spacer disposed within the head member opening and moveable between a spacer first position and a spacer second position; and a rotatable member disposed in the inner chamber and along an axis between the central axis and the head member distal side, the rotatable member defining a rotatable member gear and a cam contacting the spacer such that rotational movement of the rotatable member moves the spacer from its spacer first position to its spacer second position.

Another example hip arthroplasty trial device comprises a head member having a central axis, defining an inner chamber, and having a head member outer surface, a head member proximal side, and a head member distal side, the head member outer surface defining a head member cavity extending into the head member along an axis between the central axis and the head member proximal side to a base wall defining a base wall opening, the head member proximal side defining a head member opening that provides access to the inner chamber; a spacer disposed within the head member opening and moveable between a spacer first position and a spacer second position; and a rotatable member disposed in the inner chamber and along an axis between the central axis and the head member distal side, the rotatable member defining a rotatable member gear and a cam contacting the spacer such that rotational movement of the rotatable member moves the spacer from its spacer first position to its spacer second position, the rotatable member gear partially disposed within the head member cavity.

An example hip arthroplasty trial system comprises a hip arthroplasty trial device and a driver. The hip arthroplasty trial device comprises a head member, a spacer disposed in and movable within an opening defined by the head member, a rotatable member defining a gear and a cam adapted to translate the spacer upon rotation of the rotatable member, and a locking member. The head member defines a cavity providing access to the gear defined by the rotatable member. The driver comprises a handle, a main body extending from the handle, and a driver gear disposed on the handle. The driver gear is sized and configured to be received by the cavity of the head member and has teeth that are sized and configured to mesh with teeth of the gear defined by the rotatable member.

Another example hip arthroplasty trial system comprises a hip arthroplasty trial device and a driver. The hip arthroplasty trial device comprises a head member, a spacer disposed in and movable within an opening defined by the head member, a rotatable member defining a gear and a cam adapted to translate the spacer upon rotation of the rotatable member, and a locking member. The head member defines a cavity providing access to the gear defined by the rotatable member. The base of the cavity defines an opening. The driver comprises a handle, a main body extending from the handle, a driver gear disposed on the handle, and a terminal projection extending from the main body and axially beyond the driver gear such that driver gear is positioned axially between the terminal projection and the handle. The driver gear is sized and configured to be received by the cavity of the head member and has teeth that are sized and configured to mesh with teeth of the gear defined by the rotatable member. The terminal projection is sized and configured to be received by the opening defined by the base of the cavity defined by the head member.

Another example hip arthroplasty trial system comprises a hip arthroplasty trial device and a driver. The hip arthroplasty trial device comprises a head member, a spacer disposed in and movable within an opening defined by the head member, a rotatable member defining a gear and a cam adapted to translate the spacer upon rotation of the rotatable member, and a locking member. The head member defines a cavity providing access to the gear defined by the rotatable member. The base of the cavity defines an opening. The driver comprises a handle, a main body extending from the handle, a driver gear disposed on the handle, a terminal projection extending from the main body and axially beyond the driver gear such that driver gear is positioned axially between the terminal projection and the handle, and a projection that extends away from and orthogonal to a longitudinal axis of main body. The driver gear is sized and configured to be received by the cavity of the head member and has teeth that are sized and configured to mesh with teeth of the gear defined by the rotatable member. The terminal projection is sized and configured to be received by the opening defined by the base of the cavity defined by the head member.

Another example hip arthroplasty trial system comprises a hip arthroplasty trial device, comprising a head member having a central axis, defining an inner chamber, and having a head member outer surface, a head member proximal side, and a head member distal side, the head member outer surface defining a head member cavity extending into the head member along an axis between the central axis and the head member proximal side to a base wall defining a base wall opening, the head member proximal side defining a head member opening that provides access to the inner chamber, a spacer disposed within the head member opening and moveable between a spacer first position and a spacer second position, and a rotatable member disposed in the inner chamber and along an axis between the central axis and the head member distal side, the rotatable member defining a rotatable member gear and a cam contacting the spacer such that rotational movement of the rotatable member moves the spacer from its spacer first position to its spacer second position, the rotatable member gear partially disposed within the head member cavity; and a driver comprising a handle, a main body extending from the handle, and a driver gear disposed on the main body and axially spaced from the handle, the driver gear sized and configured to be releasably disposed in the head member cavity and meshed with the rotatable member gear.

Additional understanding of the example hip arthroplasty trial devices and hip arthroplasty trial systems can be obtained by review of the detailed description, below, and the appended drawings.

BRIEF DESCRIPTION OF THE DRAWINGS

FIG. 19 is a perspective view of the driver of the hip arthroplasty trial system illustrated in FIG. 16.

FIG. 20 is a side view of the driver of the hip arthroplasty trial system illustrated in FIG. 16.

FIG. 21 is an end view of the driver of the hip arthroplasty trial system illustrated in FIG. 16.

FIG. 24 is a top view of the hip arthroplasty trial system illustrated in FIG. 16. The hip arthroplasty trial device is releasably attached to the femoral stem, which is partially broken away. The driver and the hip arthroplasty trial device are each illustrated in their respective first positions.

FIG. 24A is a sectional view of the hip arthroplasty trial device and femoral stem illustrated in FIG. 24, taken along line 24A-24A.

FIG. 25 is a top view of the hip arthroplasty trial system illustrated in FIG. 16. The hip arthroplasty trial device is releasably attached to the femoral stem, which is partially broken away. The driver and the hip arthroplasty trial device are each illustrated in their respective second positions.

FIG. 25A is a sectional view of the hip arthroplasty trial device and femoral stem illustrated in FIG. 25, taken along line 25A-25A.

DETAILED DESCRIPTION

Figure 1:
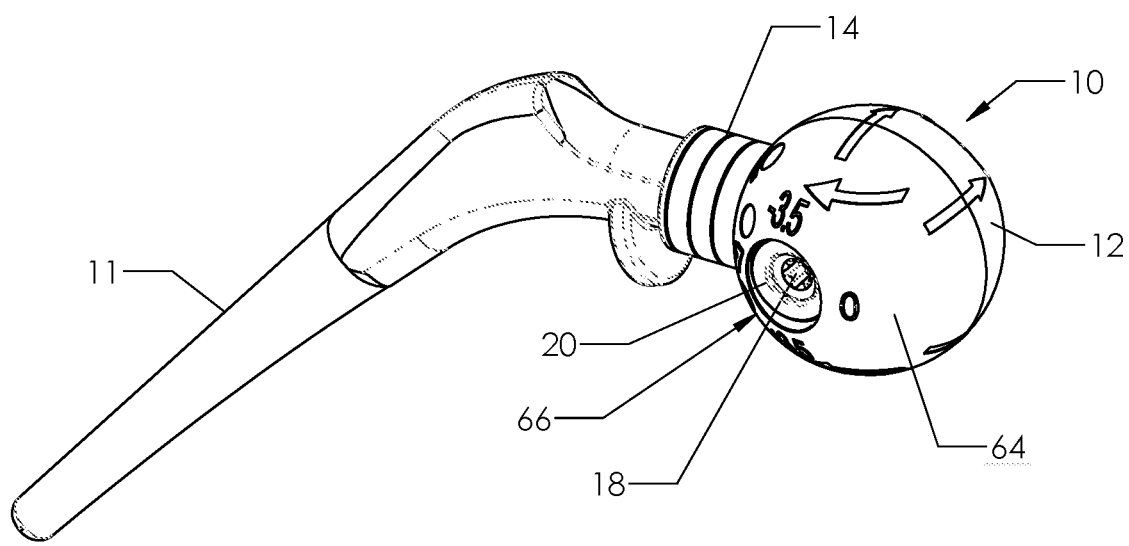
FIG. 1 illustrates a first example hip arthroplasty trial device releasably attached to a femoral stem.

The following detailed description and the appended drawings describe and illustrate example hip arthroplasty trial devices and hip arthroplasty trial systems. The description and illustration of these examples are provided to enable one skilled in the art to make and use a hip arthroplasty trial device and a hip arthroplasty trial system according to an embodiment. They are not intended to limit the scope of the claims in any manner.

FIGS. 1, 2, 3, 4, 5, 6, 7, 8, 9, 10, 11, 12, 12A, 13, 13A, 14, 14A, 15, and 15A illustrate an example hip arthroplasty trial device 10, or a component thereof, for use in hip arthroplasty. FIGS. 1, 2, 11, 12, 12A, 13, 13A, 14, 14A, 15, and 15A illustrate the hip arthroplasty trial device 10 releasably attached to a femoral stem 11. The hip arthroplasty trial device 10 has a head member 12, a spacer 14, a rotatable member 16, a drive gear 18, a washer 20, an o-ring 22, and a locking member 24.

Figure 2:
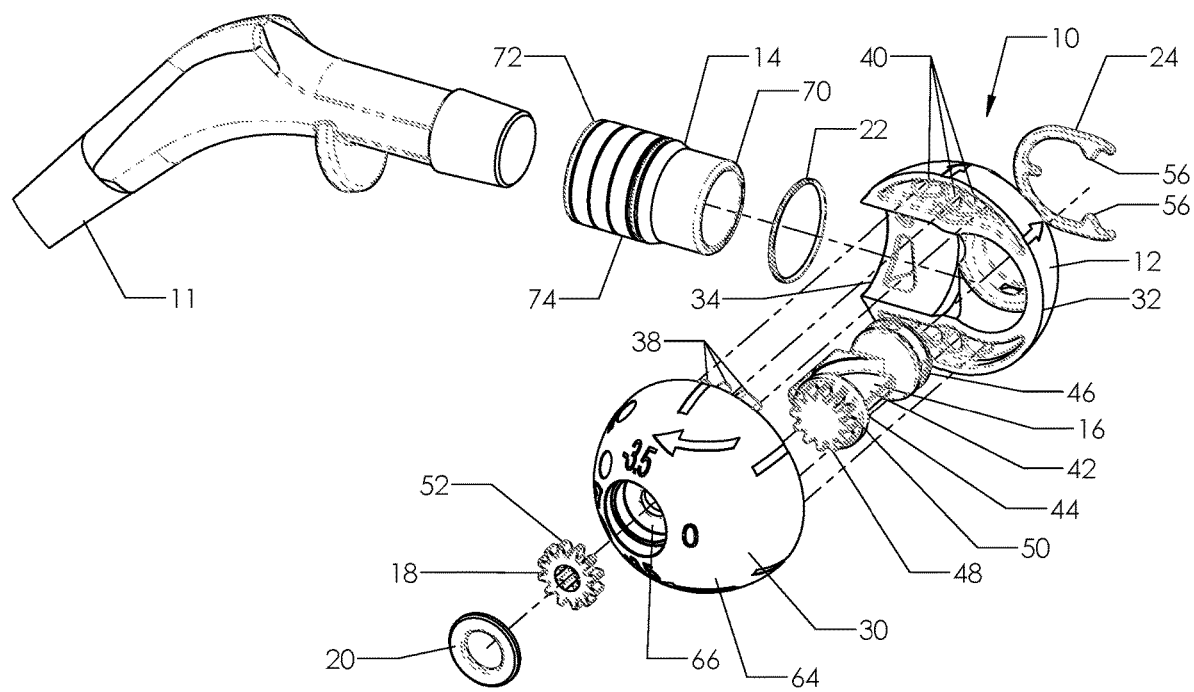
FIG. 2 is an exploded view of the hip arthroplasty trial device and femoral stem illustrated in FIG. 1.
Figure 3:
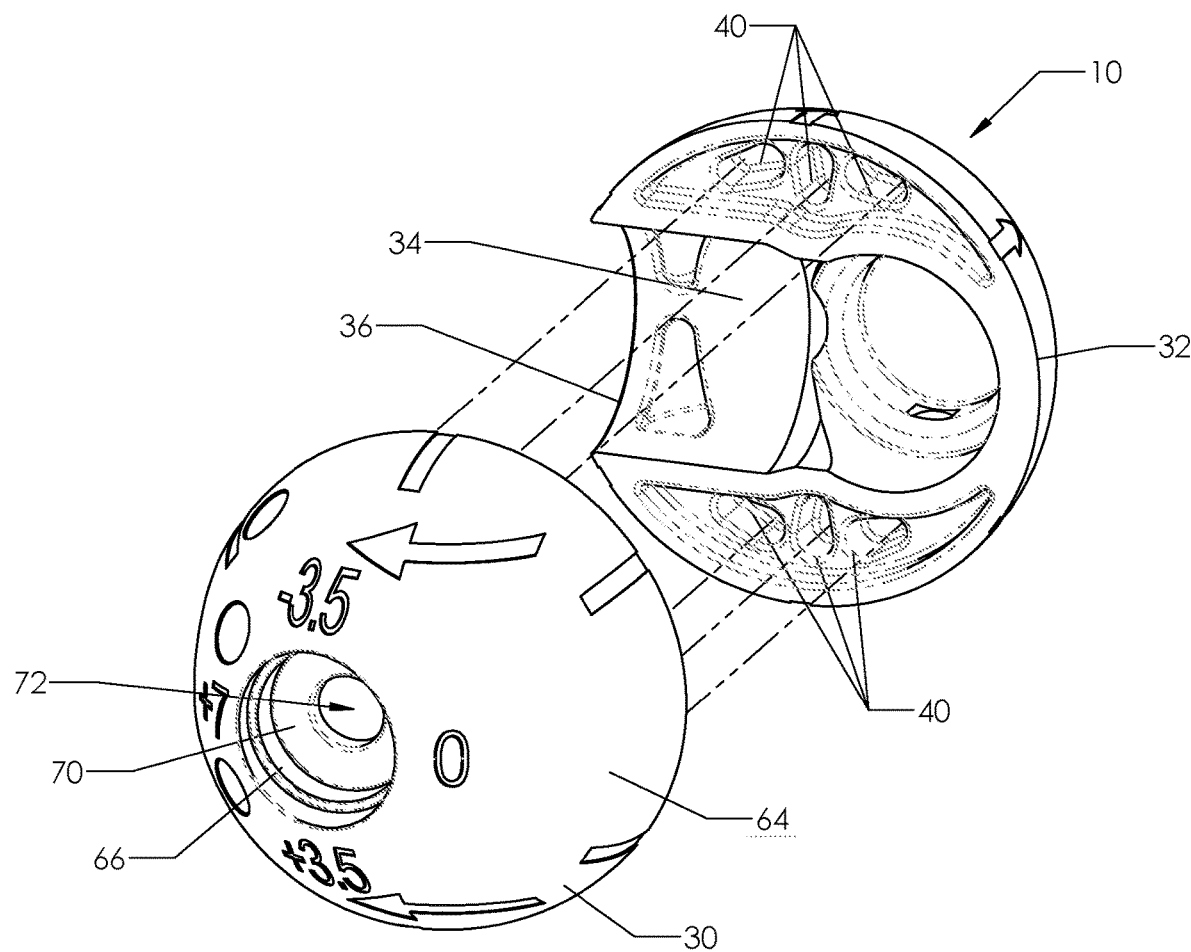
FIG. 3 is an exploded view of the head member of the hip arthroplasty trial device illustrated in FIG. 1.
Figure 4:
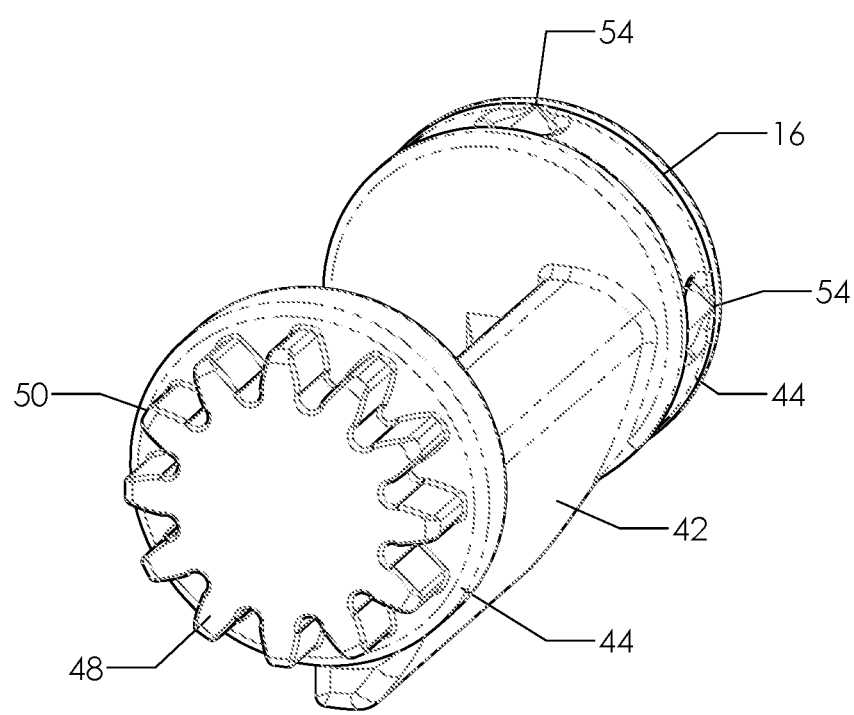
FIG. 4 is a perspective view of the rotatable member of the hip arthroplasty trial device illustrated in FIG. 1.

As best illustrated in FIGS. 2 and 3, the head member 12 comprises separable first 30 and second 32 head member portions that cooperatively define an inner chamber 34 within which the rotatable member 16 is disposed. First 30 and second 32 head member portions also cooperatively define opening 36 that provides access to the inner chamber 34 and within which spacer 14 is disposed. The first head member portion 30 defines a series of posts 38 that are releasably received by a series of mating chambers 40 defined by the second head member portion 32. Posts 38 and chambers 40 have a friction fit that allows the first 30 and second 32 head member portions to snap together to form the head member 30.

Figure 5:
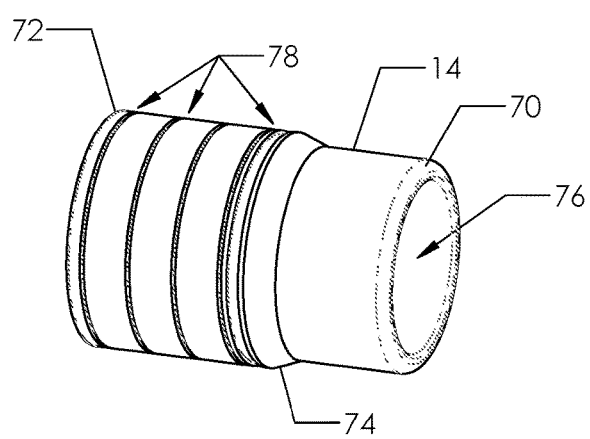
FIG. 5 is a perspective view of the spacer of the hip arthroplasty trial device illustrated in FIG. 1.
Figure 6:
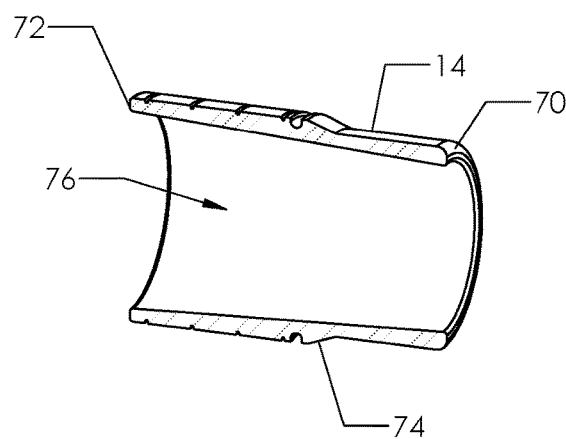
FIG. 6 is a sectional view of the spacer of the hip arthroplasty trial device illustrated in FIG. 1, taken along the central lengthwise axis of the spacer.
Figure 7:
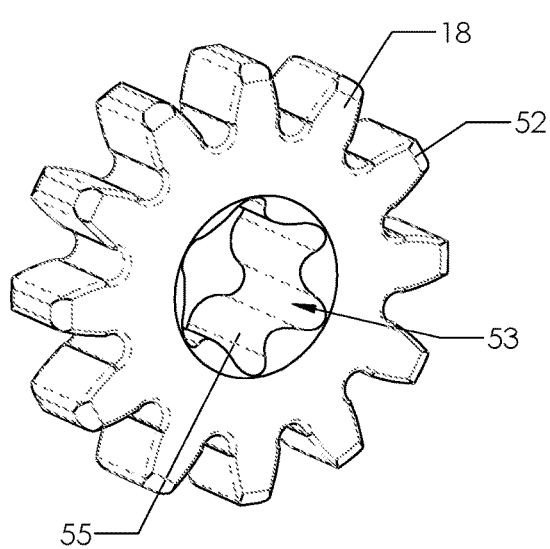
FIG. 7 is a perspective view of the drive gear of the hip arthroplasty trial device illustrated in FIG. 1.

Spacer 14 is disposed within opening 36 and is moveable between a spacer first position, a spacer second position, a spacer third position, and a spacer fourth position relative to the head member 12. As best illustrated in FIGS. 5 and 6, the spacer 14 has a spacer first end 70, a spacer second end 72, and a spacer main body 74 that defines a spacer passageway 76 and a plurality of spacer grooves 78. The spacer passageway 76 extends from the spacer first end 70 to the spacer second end 72 and tapers from the spacer second end 72 to the spacer first end 70. Each groove of the plurality of spacer grooves 78 extends into the spacer main body 74 and is located a distance from the spacer first end 70.

The rotatable member 16 defines a cam 42 adapted to translate the spacer 14 upon rotation of the rotatable member 16. The rotatable member 16 defines first 44 and second 46 bosses that seat in corresponding grooves of the first 30 and second 32 head member portions, respectively. The first boss 44 defines a gear 48 having teeth 50 that mesh with teeth 52 of the drive gear 18. The second boss 46 defines a series of pockets 54, each of which is sized and configured to receive projections 56 defined by the locking member 24.

Figure 8:
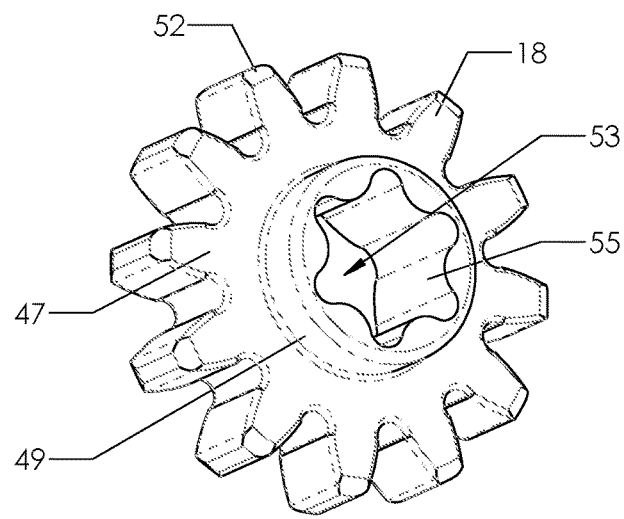
FIG. 8 is another perspective view of the drive gear of the hip arthroplasty trial device illustrated in FIG. 1.
Figure 9:
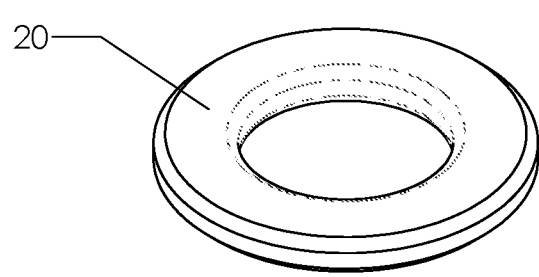
FIG. 9 is a perspective view of a washer of the hip arthroplasty trial device illustrated in FIG. 1.
Figure 10:
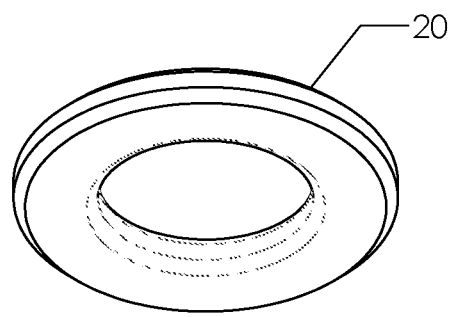
FIG. 10 is another perspective view of a washer of the hip arthroplasty trial device illustrated in FIG. 1.

Drive gear 18 defines 52 teeth sized and configured to mesh with teeth 50 of gear 48 defined by rotatable member 17. As best illustrated in FIG. 8, a first side 47 of drive gear 18 defines circumferential projection 49 that extends from first side 47 and is sized and configured to be received by opening 72 at base wall 70 of cavity 66 defined by head member 12. Drive gear 18 also defines passageway 53 bounded by wall 55 having structure sized and configured to receive and engage with a driver.

Figure 11:
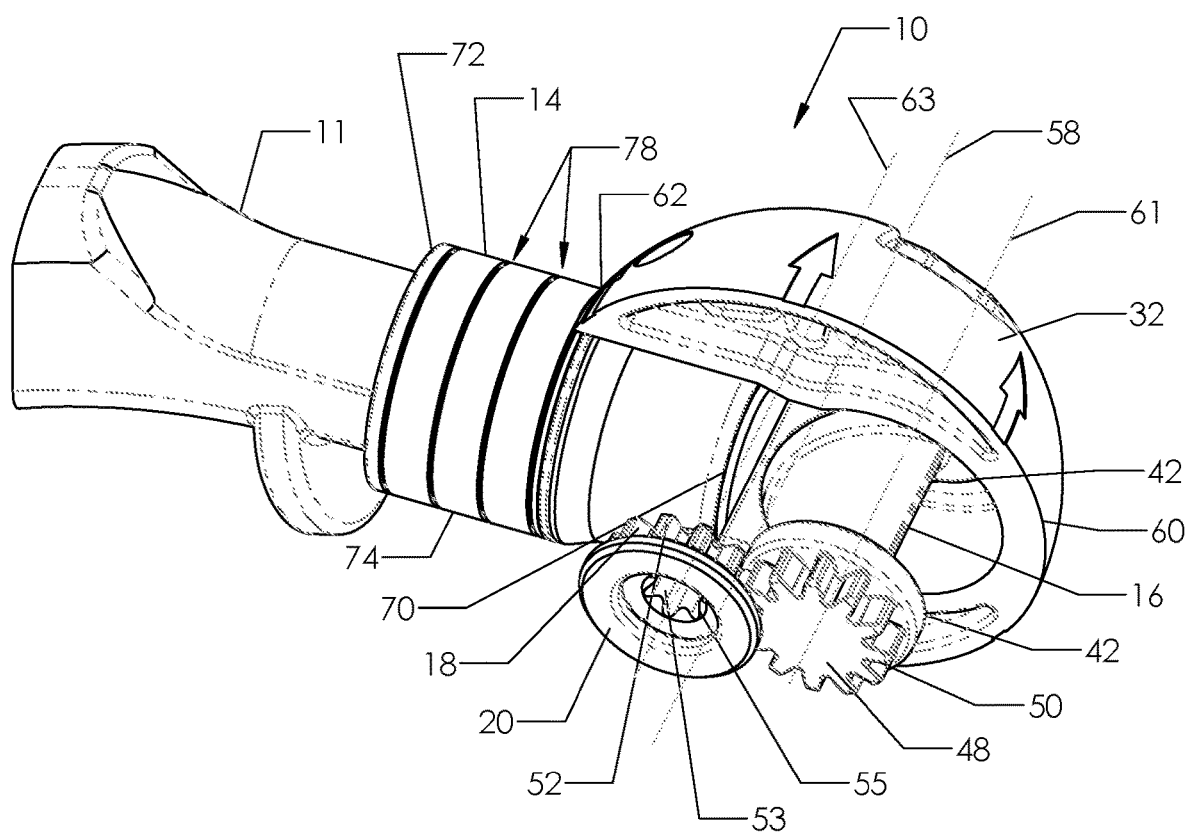
FIG. 11 is a partial sectional view of the hip arthroplasty trial device illustrated in FIG. 1 disposed on the femoral stem, which is partially broken away.
Figure 12:
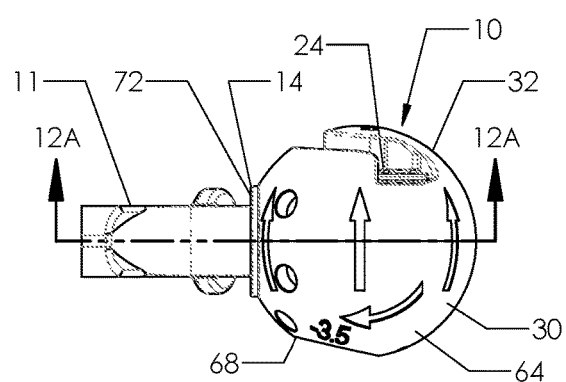
FIG. 12 is a top view of the hip arthroplasty trial device illustrated in FIG. 1 releasably attached to the femoral stem, which is partially broken away. The hip arthroplasty trial device is shown in the first position.
Figure 13:
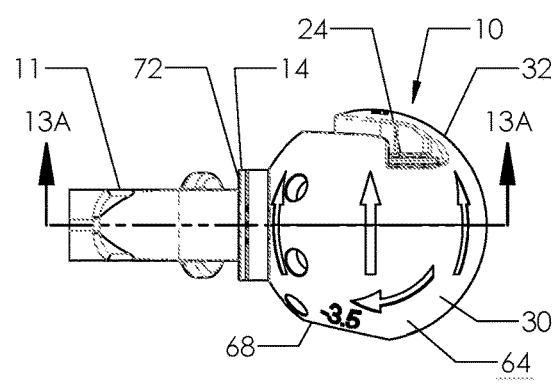
FIG. 13 is a top view of the hip arthroplasty trial device illustrated in FIG. 1 releasably attached to the femoral stem, which is partially broken away. The hip arthroplasty trial device is shown in the second position.
Figure 12A:
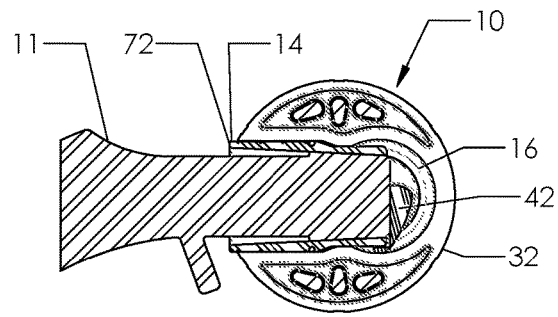
FIG. 12A is a sectional view of the hip arthroplasty trial device and femoral stem illustrated in FIG. 12, taken along line 12A-12A.
Figure 13A:
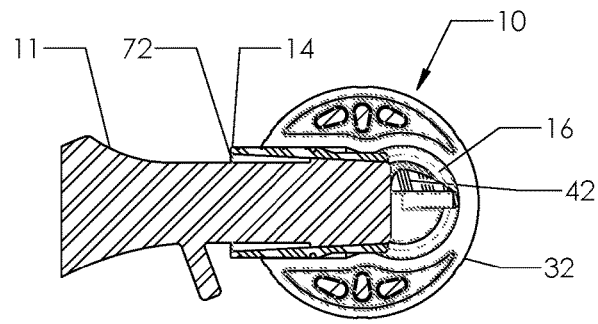
FIG. 13A is a sectional view of the hip arthroplasty trial device and femoral stem illustrated in FIG. 13, taken along line 13A-13A.
Figure 14:
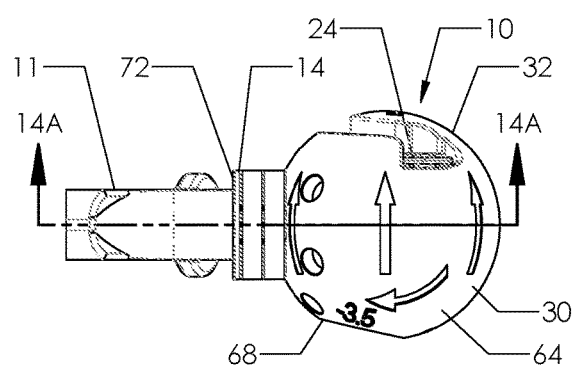
FIG. 14 is a top view of the hip arthroplasty trial device illustrated in FIG. 1 releasably attached to the femoral stem, which is partially broken away. The hip arthroplasty trial device is shown in the third position.
Figure 15:
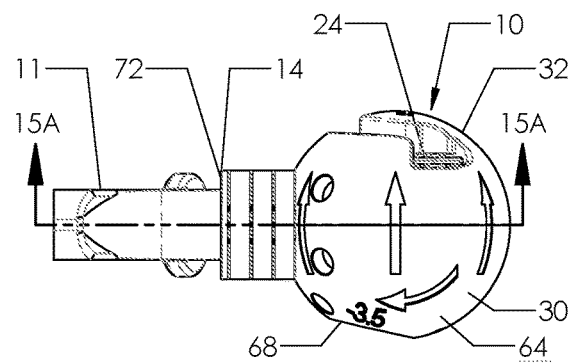
FIG. 15 is a top view of the hip arthroplasty trial device illustrated in FIG. 1 releasably attached to the femoral stem, which is partially broken away. The hip arthroplasty trial device is shown in the fourth position.
Figure 14A:
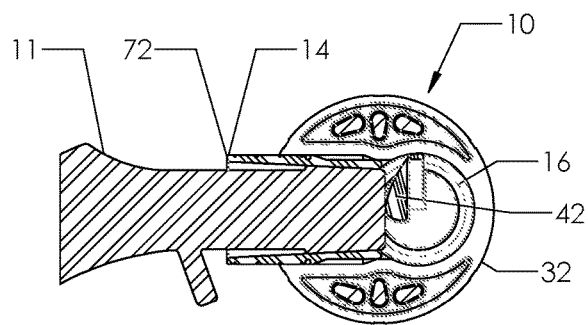
FIG. 14A is a sectional view of the hip arthroplasty trial device and femoral stem illustrated in FIG. 14, taken along line 14A-14A.
Figure 15A:
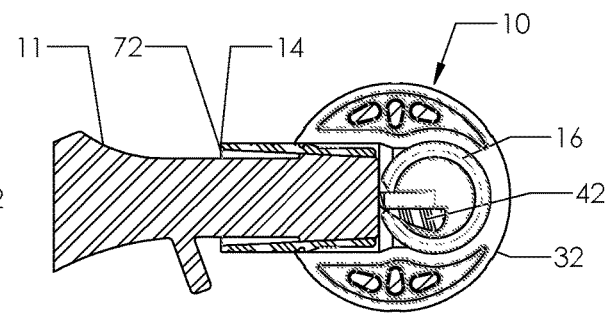
FIG. 15A is a sectional view of the hip arthroplasty trial device and femoral stem illustrated in FIG. 15, taken along line 15A-15A.
Figure 16:
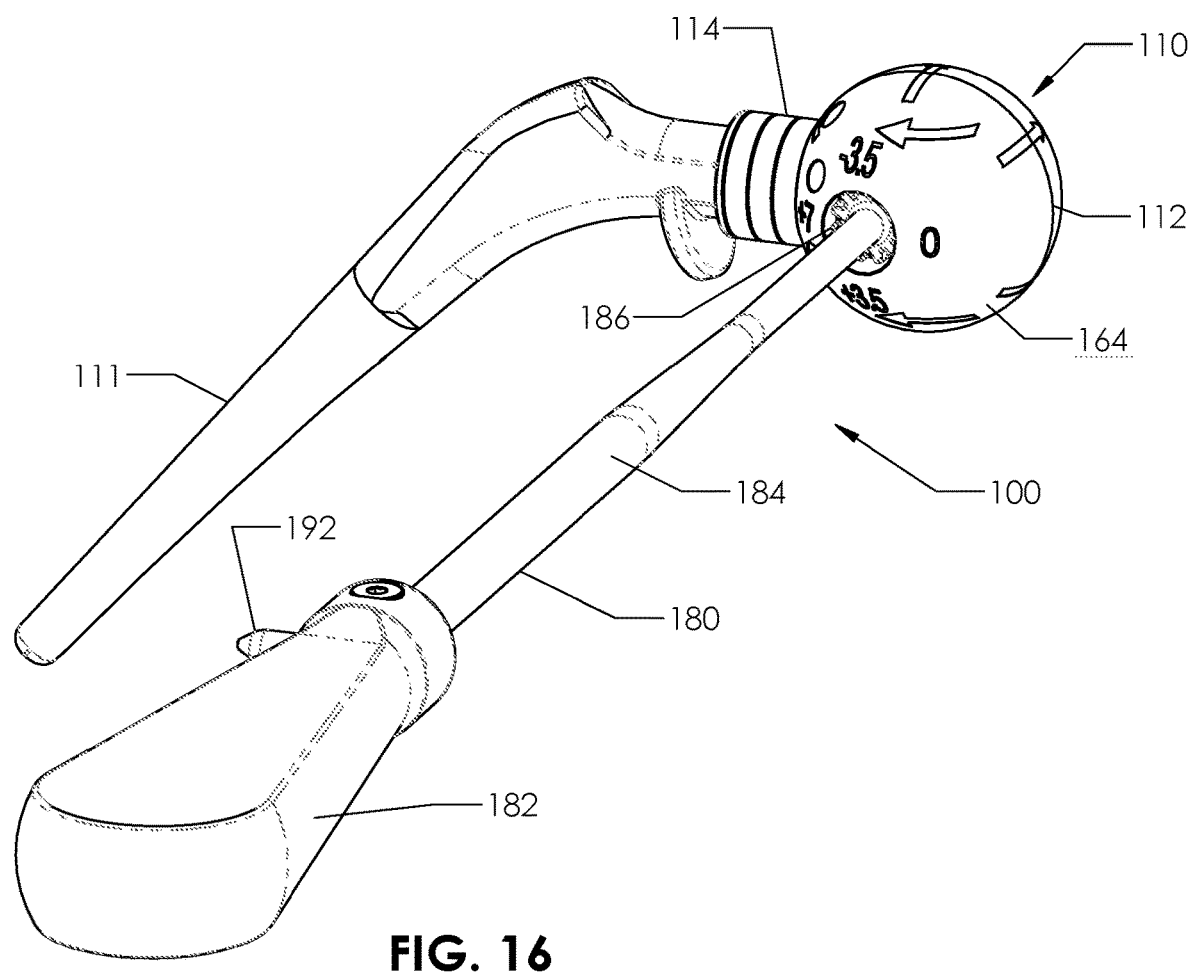
FIG. 16 illustrates a first example hip arthroplasty trial system. The hip arthroplasty trial device of the hip arthroplasty trial system is releasably attached to a femoral stem.
Figure 17:
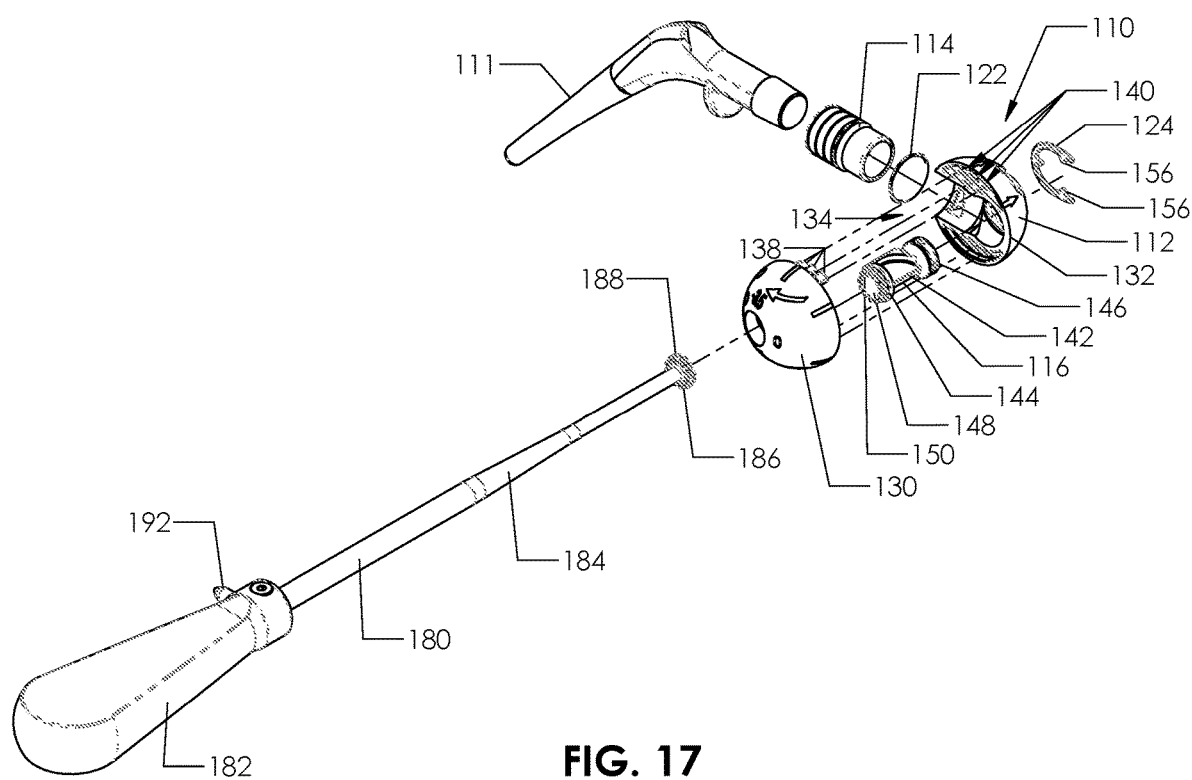
FIG. 17 is an exploded view of the hip arthroplasty trial system and femoral stem illustrated in FIG. 16.
Figure 18:
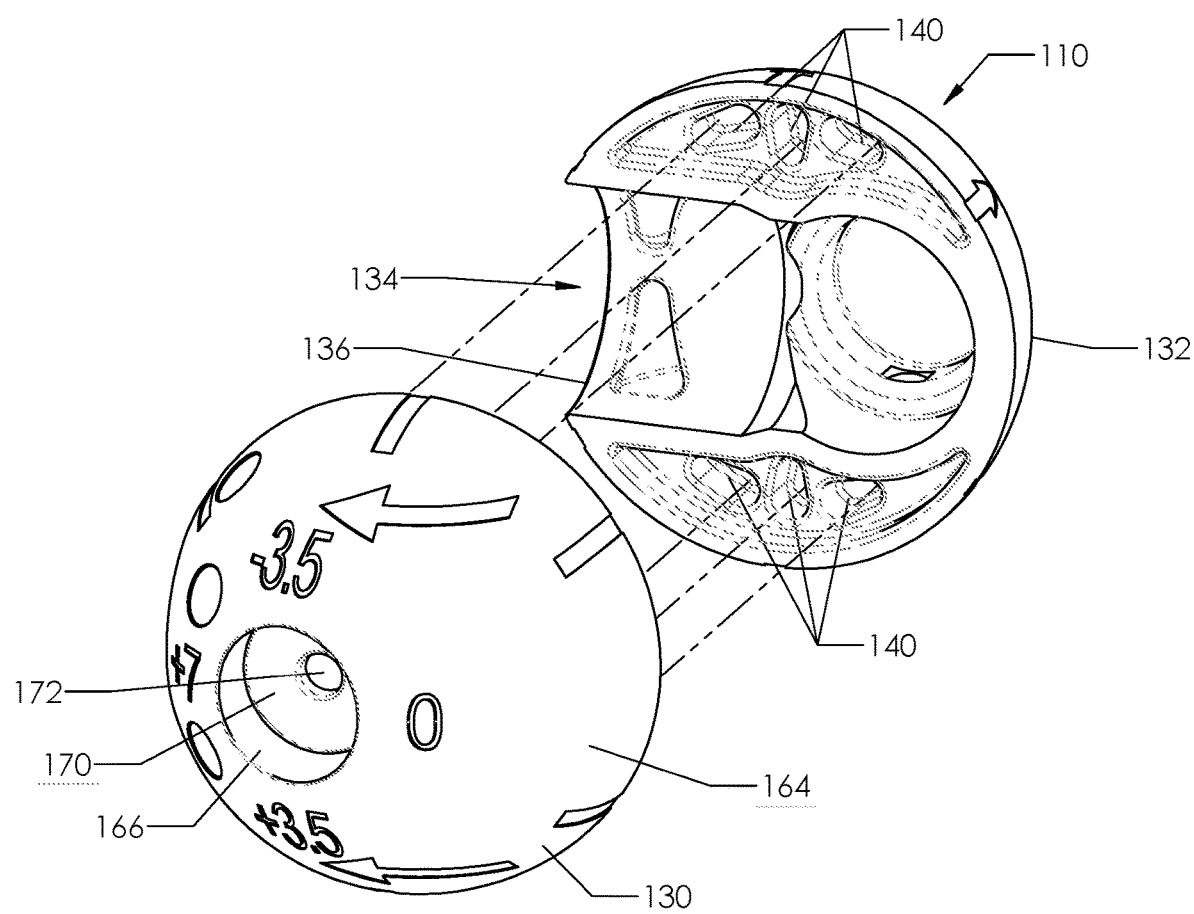
FIG. 18 is an exploded view of the head member of the hip arthroplasty trial device of the hip arthroplasty trial system illustrated in FIG. 16.

The inclusion of drive gear 18 and gear 48 on rotatable member 16 enables an offset positioning of the adjustment mechanism by which rotatable member 16 is rotated to move cam 42 and, ultimately, translate the spacer 14. As best illustrated in FIG. 11, gear 48 is positioned on an axis 61 that lies between the central axis 58 of head member 12 and the distal side 60 of head member 12 and drive gear 18 is positioned on an axis 63 between the central axis 58 and proximal side 62 of head member 12, which defines opening 36. This placement of drive gear 18, which is offset from central axis 58 extending through the head member 12, is advantageous at least because it provides greater access to the adjustment mechanism in the relatively tight space available during use of the hip arthroplasty trial device 10 during a hip arthroplasty procedure, allowing adjustments to be made in situ, with all arthroplasty components assembled. Also, this offset positioning of drive gear 18 and rotatable member 16, with drive gear lying on one axis 61 offset from and on one side of central axis 58 and rotatable member and gear 48 lying on another axis 63 offset from and on another, opposite side of central axis 58, is critical to use of the hip arthroplasty trial device 10 across a range of head sizes, including smaller head sizes (e.g., 28 mm and 32 mm heads). This structural configuration provides adjustability in hip arthroplasty trial devices that, to date, have not been able to include adjustment mechanisms. Current adjustable head trial devices include a centrally located cam, which cannot be positioned within smaller head sizes.

As best illustrated in FIGS. 1, 2, and 3, outer surface 64 of head member 12 defines cavity 66 that provides access to drive gear 18. An optional washer 20 is disposed in cavity 66 to retain drive gear 18 in position. Cavity 66 is sized and configured to receive a driver, such as a Torx driver or other suitable driver, defining structure to engage and rotate drive gear 18 which, in turn, results in rotation of rotatable member 16 and translation of spacer 18. Also, as best illustrated in FIGS. 12, 13, 14, and 15, outer surface 64 is largely spherical, but defines facet 68 where outer surface 64 forms cavity 66.

In use, a driver is inserted into cavity 66 to engage and rotate drive gear 18 in a clockwise direction. In turn, this rotation of drive gear 18 results in counterclockwise rotation of gear 48 on rotatable member 16. As gear 48 is defined by rotatable member 16, rotation of gear 48 produces rotation of rotatable member 16 and cam 42 which, in turn, results in translation of spacer relative to the head member 12. Rotation of drive gear 18 in this manner moves spacer 14 from a spacer first position relative to the head member 12, illustrated in FIGS. 12 and 12A, to a spacer second position relative to the head member 12, illustrated in FIGS. 13 and 13A. Additional rotation of drive gear 18 in this manner moves spacer 14 from the spacer second position to a spacer third position relative to the head member 12, illustrated in FIGS. 14 and 14A. Similarly, additional rotation of drive gear 18 in this manner moves spacer 14 from the spacer third position to a spacer fourth position relative to the head member 12, illustrated in FIGS. 15 and 15A.

The inclusion of gear 48 and drive gear 18, the offset positioning of drive gear 18, and the faceted structure of the outer surface 64 of the head member 12 cooperate to provide significant advantages over existing adjustable hip arthroplasty trial devices. For example, the hip arthroplasty trial device 10 will accommodate shorter neck trunnions, sizes of which vary by manufacturer. This allows the hip arthroplasty trial device 10 to be used across a wider array of femoral stems, which will likely increase its adoption rate. Also, the overall structure of the hip arthroplasty trial device 10 lends itself to a construction made of disposable components, such as plastic components, eliminating the need for disassembly, cleaning, sterilization, and reuse that is required for existing devices.

FIGS. 16, 17, 18, 19, 20, 21, 22, 23, 24, 24A, 25, 25A, 26, 26A, 27, and 27A illustrate an example hip arthroplasty trial system 100, or a component thereof, for use in hip arthroplasty. Hip arthroplasty trial system 100 includes hip arthroplasty trial device 110 and driver 180. FIGS. 16, 17, 22, 23, 24, 24A, 25, 25A, 26, 26A, 27, and 27A illustrate the hip arthroplasty trial device 110 of the hip arthroplasty trial system 100 releasably attached to a femoral stem 111.

The hip arthroplasty trial device 110 is similar to hip arthroplasty trial device 10 described above, except as detailed below. Thus, hip arthroplasty trial device 110 has a head member 112, a spacer 114, a rotatable member 116, an o-ring 122, and a locking member 124. The head member 112 comprises separable first 130 and second 132 head member portions that cooperatively define an inner chamber 134 within which the rotatable member 116 is disposed. First 130 and second 132 head member portions also cooperatively define opening 136 that provides access to the inner chamber 134 and within which spacer 114 is disposed. The first head member portion 130 defines a series of posts 138 that are releasably received by a series of mating chambers 140 defined by the second head member portion 132. Posts 138 and chambers 140 have a friction fit that allows the first 130 and second 132 head member portions to snap together to form the head member 130.

Spacer 114 is disposed within opening 136 and is moveable between a spacer first position, a spacer second position, a spacer third position, and a spacer fourth position relative to the head member 112. Rotatable member 116 defines a cam 142 adapted to translate the spacer 114 upon rotation of the rotatable member 116. The rotatable member 116 defines first 144 and second 146 bosses that seat in corresponding grooves of the first 130 and second 132 head member portions, respectively. The first boss 142 defines a gear 148 having teeth 150 that mesh with teeth 188 of the driver gear 186, as described in detail below. The second boss 146 defines a series of pockets 154, each of which is sized and configured to receive projections 156 defined by the locking member 124.

Figure 22:
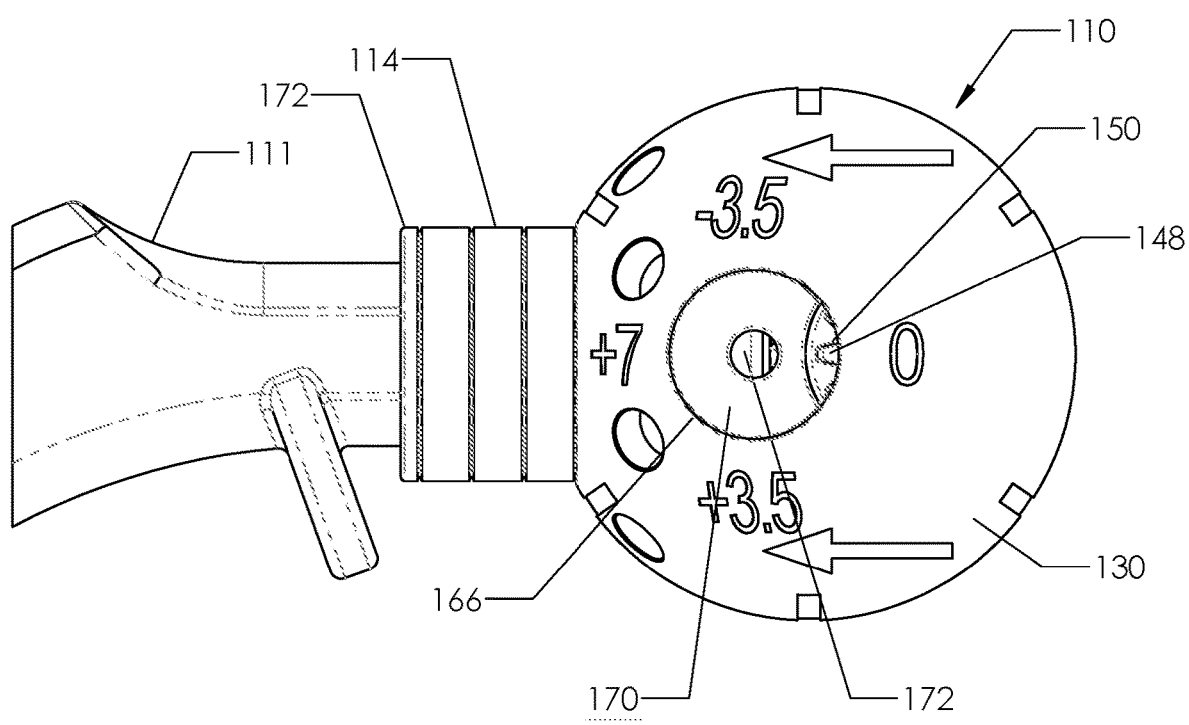
FIG. 22 is a side view of the hip arthroplasty trial device of the hip arthroplasty trial system illustrated in FIG. 16. The hip arthroplasty trial device is releasably attached to the femoral stem, which is partially broken away.

As best illustrated in FIGS. 22, outer surface 164 of head member 112 defines cavity 166 that provides access to gear 148 on rotatable member 116. Cavity 166 is sized and configured to receive driver gear 186 in a manner that allows teeth 188 of driver gear 186 to mesh with teeth 150 of gear 148 on rotatable member 116. Thus, driver gear 186 is sized and configured to be releasably disposed in cavity 166 and meshed with the gear 148 on rotatable member 116. The positioning of cavity 166 provides offset positioning of the adjustment mechanism by which rotatable member 116 is rotated to move cam 142 and, ultimately, translate the spacer 114. As best illustrated in FIG. 22, gear 148 is positioned between the central axis 158 of head member 112 and the distal side 160 of head member 112 and cavity 166 is positioned between the central axis 158 and proximal side 162 of head member 112, which defines opening 136. This placement of cavity 166, which is offset from central axis 158 extending through the head member 112, is advantageous at least because it provides offset access for driver 180 and driver gear 186, which facilitates adjustment within the limited space available during use of the hip arthroplasty trial system 100. Base wall 170 of cavity 166 defines opening 172 that is sized and configured to receive terminal projection 190 of driver 180.

As best illustrated in FIGS. 24, 25, 26, and 27, outer surface 164 is largely spherical, but defines facet 168 where outer surface 164 forms cavity 166.

Figure 23:
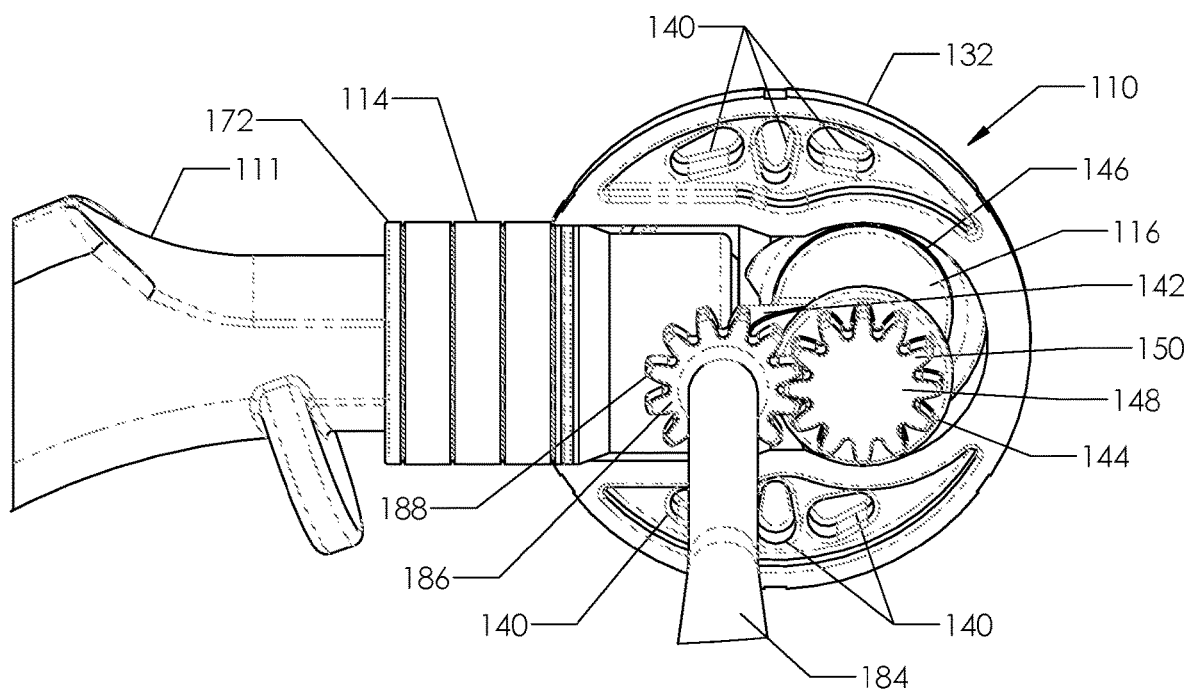
FIG. 23 is a partial sectional view of the hip arthroplasty trial device of the hip arthroplasty trial system illustrated in FIG. 16. The hip arthroplasty trial device is releasably attached to the femoral stem, which is partially broken away.

As best illustrated in FIGS. 19, 20, and 21, driver 180 is an elongate member having a handle 182, a main body 184 extending from the handle 182, and a driver gear 186 disposed on the main body 184 and axially spaced from the handle 182. As best illustrated in FIG. 23, driver gear 186 defines teeth 188 that are sized and configured to mesh with teeth 150 of gear 148 defines by rotatable member 116. A terminal projection 190 extends from the main body 184 and axially beyond driver gear 186 such that driver gear 186 is positioned axially between terminal projection 190 and handle 182. Terminal projection 190 is sized and configured to be received by opening 172 at base wall 170 of cavity 166, ensuring proper seating of driver gear 186 within cavity 166 during use of hip arthroplasty trial system.

Figure 26:
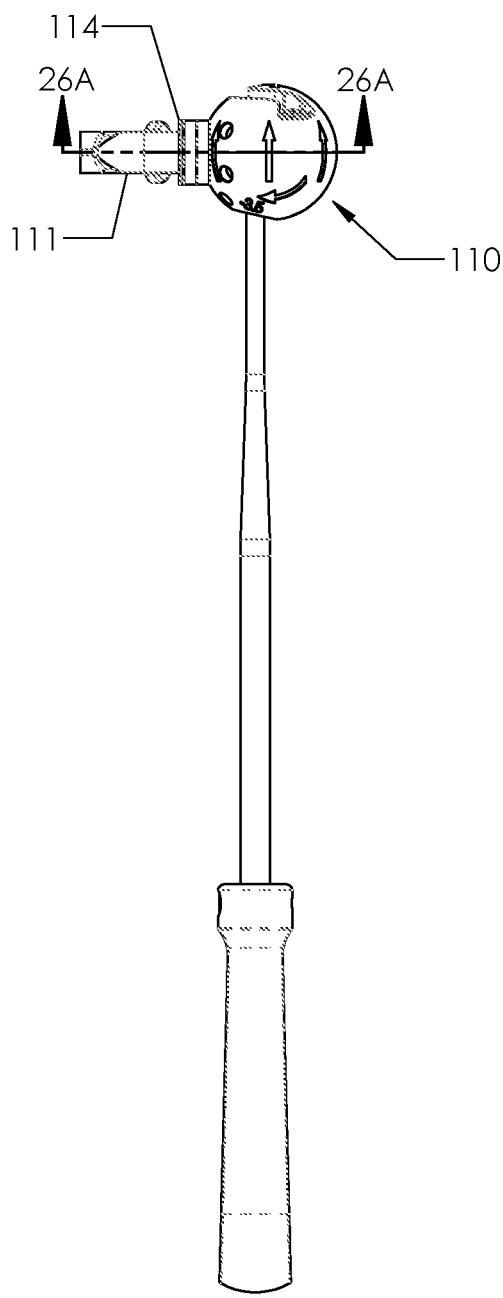
FIG. 26 is a top view of the hip arthroplasty trial system illustrated in FIG. 16. The hip arthroplasty trial device is releasably attached to the femoral stem, which is partially broken away. The driver and the hip arthroplasty trial device are each illustrated in their respective third positions.
Figure 27:
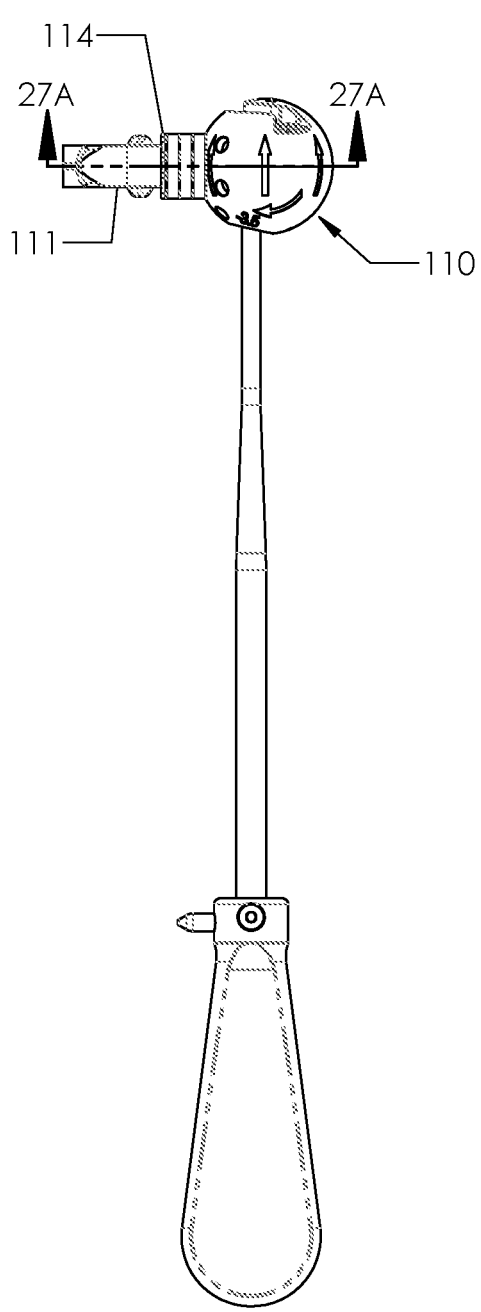
FIG. 27 is a top view of the hip arthroplasty trial system illustrated in FIG. 16. The hip arthroplasty trial device is releasably attached to the femoral stem, which is partially broken away. The driver and the hip arthroplasty trial device are each illustrated in their respective fourth positions.
Figure 26A:
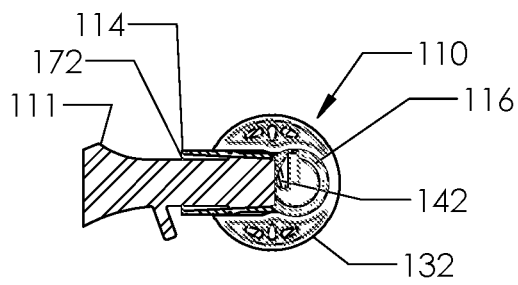
FIG. 26A is a sectional view of the hip arthroplasty trial device and femoral stem illustrated in FIG. 26, taken along line 26A-26A.
Figure 27A:
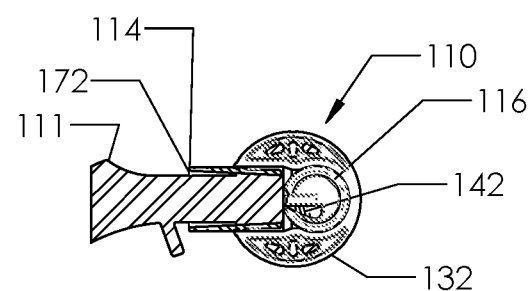
FIG. 27A is a sectional view of the hip arthroplasty trial device and femoral stem illustrated in FIG. 27, taken along line 27A-27A.

Driver 180 also includes projection 192 that extends away from and orthogonal to a longitudinal axis of main body 184. As best illustrated in FIGS. 24, 25, 26, and 27, projection 192 provides a visual indicator to a user of the hip arthroplasty trial system or the rotational position of the driver 180 relative to an initial position of the driver 180. For example, in FIG. 24, driver 180 is in a first or initial driver position in which the driver gear 186 is disposed in cavity 166 and meshed with gear 148 of rotatable member 116. Rotation has not yet been initiated, though, keeping spacer 114 in its first spacer position, as best illustrated in FIG. 24A. Projection 192 is in a first rotational position. In FIG. 25, driver 180 has been rotated to a second driver position, which has rotated driver gear 186. As a result, gear 148 of rotatable member 116 has rotated, causing movement of cam 142 that, in turn, translates spacer 114 to its second spacer position, as best illustrated in FIG. 25A. Projection 192 is in a second rotational position, 90 degrees offset from the first rotational position. In FIG. 26, driver 180 has been rotated to a third driver position, which has rotated driver gear 186 further. As a result, gear 148 of rotatable member 116 has rotated further, causing further movement of cam 142 that, in turn, translates spacer 114 to its third spacer position, as best illustrated in FIG. 26A. Projection (not visible in FIG. 26) is in a third rotational position, 180 degrees offset from the first rotational position. In FIG. 27, driver 180 has been rotated to a fourth driver position, which has rotated driver gear 186 further. As a result, gear 148 of rotatable member 116 has rotated further, causing further movement of cam 142 that, in turn, translates spacer 114 to its fourth spacer position, as best illustrated in FIG. 27A. Projection 192 is in a fourth rotational position, 270 degrees offset from the first rotational position.

All components of the hip arthroplasty trial devices and hip arthroplasty trial system can be formed of any suitable materials. It is noted, though, that the structural configurations of the hip arthroplasty trial devices described herein facilitate use of plastics for the trial devices, making the trial devices suitable for single use and eliminating the need for disassembly, cleaning, sterilization, and reuse that is required for existing devices.

Those with ordinary skill in the art will appreciate that various modifications and alternatives for the described and illustrated examples can be developed considering the overall teachings of the disclosure. Accordingly, the structural arrangements disclosed are intended to be illustrative only and not limiting as to the scope of the invention, which is to be given the full breadth of the appended claims and any and all equivalents thereof.

What is claimed is:

1. A hip arthroplasty trial device, comprising:
   a head member having a central axis, defining an inner chamber, and having a head member outer surface, a head member proximal side, and a head member distal side, the head member outer surface defining a head member cavity extending into the head member and along an axis between the central axis and the head member proximal side, the head member proximal side defining a head member opening that provides access to the inner chamber;
   a spacer disposed within the head member opening and moveable between a spacer first position and a spacer second position; and
   a rotatable member disposed in the inner chamber and along an axis between the central axis and the head member distal side, the rotatable member defining a rotatable member gear and a cam contacting the spacer such that rotational movement of the rotatable member moves the spacer from its spacer first position to its spacer second position.

2. The hip arthroplasty trial device of claim 1, wherein the head member cavity has a base wall defining a base wall opening.

3. The hip arthroplasty trial device of claim 2, further comprising a drive gear disposed in the head member cavity, the drive gear meshed with the rotatable member gear such that rotational movement of the drive gear causes rotational movement of the of the rotatable member.

4. The hip arthroplasty trial device of claim 3, wherein the drive gear has a first side defining a circumferential projection that extends into the base wall opening.

5. The hip arthroplasty trial device of claim 4, further comprising a washer disposed in the head member cavity and over the drive gear.

6. The hip arthroplasty trial device of claim 2, wherein the rotatable member gear is partially disposed within the head member cavity.

7. The hip arthroplasty trial device of claim 2, wherein the head member outer surface defines a facet.

8. The hip arthroplasty trial device of claim 7, wherein the head member cavity extends into the head member from the facet.

9. The hip arthroplasty trial device of claim 2, wherein the head member comprises separable first and second head member portions.

10. A hip arthroplasty trial device, comprising:
    a head member having a central axis, defining an inner chamber, and having a head member outer surface, a head member proximal side, and a head member distal side, the head member outer surface defining a head member cavity extending into the head member along an axis between the central axis and the head member proximal side to a base wall defining a base wall opening, the head member proximal side defining a head member opening that provides access to the inner chamber;
    a spacer disposed within the head member opening and moveable between a spacer first position and a spacer second position; and
    a rotatable member disposed in the inner chamber and along an axis between the central axis and the head member distal side, the rotatable member defining a rotatable member gear and a cam contacting the spacer such that rotational movement of the rotatable member moves the spacer from its spacer first position to its spacer second position, the rotatable member gear partially disposed within the head member cavity.

11. The hip arthroplasty trial device of claim 10, wherein the head member outer surface defines a facet.

12. The hip arthroplasty trial device of claim 11, wherein the head member cavity extends into the head member from the facet.

13. The hip arthroplasty trial device of claim 10, wherein the head member comprises separable first and second head member portions.

14. The hip arthroplasty trial device of claim 13, wherein the first head member portion defines a post; and
wherein the second head member portion defines a recess sized and configured to receive the post.

15. A hip arthroplasty trial system, comprising:
a hip arthroplasty trial device, comprising:
a head member having a central axis, defining an inner chamber, and having a head member outer surface, a head member proximal side, and a head member distal side, the head member outer surface defining a head member cavity extending into the head member along an axis between the central axis and the head member proximal side to a base wall defining a base wall opening, the head member proximal side defining a head member opening that provides access to the inner chamber;
a spacer disposed within the head member opening and moveable between a spacer first position and a spacer second position; and
a rotatable member disposed in the inner chamber and along an axis between the central axis and the head member distal side, the rotatable member defining a rotatable member gear and a cam contacting the spacer such that rotational movement of the rotatable member moves the spacer from its spacer first position to its spacer second position, the rotatable member gear partially disposed within the head member cavity; and
a driver, comprising a handle, a main body extending from the handle, and a driver gear disposed on the main body and axially spaced from the handle, the driver gear sized and configured to be releasably disposed in the head member cavity and meshed with the rotatable member gear.

16. The hip arthroplasty trial system of claim 15, wherein the main body of the driver defines a terminal projection extending away from the main body and axially beyond the driver gear such that the driver gear is positioned axially between the terminal projection and the handle.

17. The hip arthroplasty trial system of claim 16, wherein the terminal projection is sized and configured to be disposed in the base wall opening.

18. The hip arthroplasty trial system of claim 17, wherein the main body has a longitudinal axis; and
wherein driver further comprises a projection that extends away from and orthogonal to the longitudinal axis of main body.

19. The hip arthroplasty trial system of claim 18, wherein the head member outer surface defines a facet.

20. The hip arthroplasty trial device of claim 19, wherein the head member cavity extends into the head member from the facet.

* * * * *